United States Patent [19]

Mori et al.

[11] 4,110,166

[45] Aug. 29, 1978

[54] PROCESS FOR THE PRODUCTION OF NOCARDICIN A

[75] Inventors: Shigeru Mori, Nishinomiya; Shigeyoshi Ohsawa, Takatsuki; Hatsuo Aoki, Ikeda; Hiroshi Imanaka, Osaka, all of Japan

[73] Assignee: Fujisawa Pharmaceutical Co., Ltd., Osaka, Japan

[21] Appl. No.: 742,013

[22] Filed: Nov. 15, 1976

[30] Foreign Application Priority Data

Nov. 19, 1975 [JP] Japan ................................ 50-139405

[51] Int. Cl.² ............................................... C12D 9/14
[52] U.S. Cl. ......................................... 195/96; 195/30
[58] Field of Search ......................... 195/80 R, 96, 30

[56] References Cited

U.S. PATENT DOCUMENTS 3,923,977  12/1975  Aoki et al. ..................... 195/80 R Primary Examiner—Alvin E. Tanenholtz
Attorney, Agent, or Firm—Dayton R. Stemple, Jr.

[57] ABSTRACT

Nocardicin A is produced by culturing a Nocardicin A producing microorganism in a medium containing at least one of shikimic acid, a hydroxy phenyl carboxylic acid, glycine, alanine, serine, homoserine, α-aminobutyric acid, α, β-diaminoproprionic acid and their ester, acid amide and hydrazide derivatives in a concentration of 2–0.001% by weight.

29 Claims, No Drawings

PROCESS FOR THE PRODUCTION OF NOCARDICIN A

This invention relates to an improved method for the production of the antibiotic Nocardicin A by fermentation. More particulary, it relates to an improved method for the production of the antibiotic Nocardicin A by the fermentation of nutrient media, to which an effective additive is added, with a suitable strain of Nocardicin A-producing microorganisms such as Nocardia.

Accordingly, it is an object of this invention to provide a method of increasing the yield of the antibiotic Nocardicin A in a fermentation process.

Further object of this invention is to provide a method of increasing the yield of the antibiotic Nocardicin A using relatively inexpensive, readily available chemical additives in the fermentation process.

The antibiotic Nocardicin A, an object compound of this invention is a known compound having antibacterial activities against Gram positive bacteria and negative bacteria, and is disclosed under the code name of the antibiotic FR-1923 substance in literatures, e.g. U.S. Pat. No. 3,923,977 and German Offenlegungsschrift No. 2,242,699, in which the said antibiotic is defined by the various physico-chemical properties without the chemical structure thereof, but, as the result of further investigation, its chemical structure has been identified and assigned as follows.

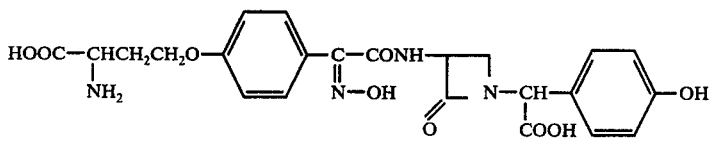

And further, it is to be noted that a process for producing the antibiotic Nocardicin A (i.e. the antibiotic FR-1923 substance) by fermentation of a microorganism belonging to the genus Nocardia is also disclosed in the above-cited United States Patent and German Offenlegungsschrift.

Microorganism to be used in this invention may include any microorganism which is capable of producing Nocardicin A. As such a microorganism, there is exemplified a Nocardicin A-producing strain belonging to the genus Nocardia.

Among such an organism, preferred one is *Nocardia uniformis* subsp. tsuyamanensis, a strain of which was deposited on June 13, 1972 with American Type Culture Collection (ATCC) located in 12301 Parklawn Dr., Rockville, Md. 20852, USA and assigned the ATCC No. 21806. This deposited *Nocardia uniformis* subsp. tsuyamanensis ATCC 21806 is now available to the public and the details thereof, i.e. the microbiological characteristics, etc. are also disclosed in the above-cited United States Patent and German Offenlegungsschrift.

It is to be understood that, for the production of the antibiotic Nocardicin A, this invention is not limited to the use of (specific) organism described herein, which is given only for illustrative purpose. Further, this invention also includes the use of natural mutants as well as artificial ones which can be derived from the microorganism as described herein in a conventional manner such as radiation with X-rays or Ultraviolet, treatment with N-methyl-N'-nitro-N-nitrosoguanidine (NTG), 2-aminopurine or nitrogen mustards, and the like.

It has been discovered that the addition of an effective additive specified below to the fermentation media can enhance the production of the antibiotic Nocardicin A.

Such effective additive include two kinds of chemical compounds and are shown as "A-group of the additive" and "B-group of the additive" for the convenience's sake of explanation as follows.

That is:

"A-group of the additive" is a compound selected from shikimic acid;

a carboxylic acid of the formula:

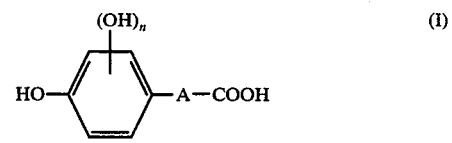

wherein A is alkylene group having hydroxy, amino, acylamino or oxo group and $n$ is an integer of 0–4;

and their derivative at the carboxy group thereof.

"B-group of the additive" is a compound selected from glycine, alanine, serine, homoserine, α-aminobutyric acid and/or α,β-diaminopropionic acid.

Accordingly, it is to be noted that the characteristics of this invention lie only in the improvement of the method for preparing Nocardicin A by culturing a Nocardicin A-producing microorganism in a fermentation medium, and said improvement is characterized by adding at least one additive selected from the compound as specified above to the fermentation medium to enhance the production of Nocardicin A. On the other hand, it is to be noted that a microorganism per se to be used and the other fermentation conditions are not characteristic in this invention and therefore these are quite conventional to the skilled in the arts.

Particulars of the above definitions of the carboxylic acid (I) will be explained as follows.

Alkylene in the alkylene having hydroxy, amino, acylamino or oxo group may be one having 1–6 carbon atoms, preferably 1–2 carbon atoms, suitable examples of which are methylene, ethylene and the like.

Acyl in the acylamino group may include aliphatic acyl, aromatic acyl and heterocycle acyl. The representative examples of said acyl may be alkanoyl having 1–6 carbon atoms, more preferably alkanoyl having 1–3 carbon atoms such as formyl, acetyl, propionyl and the like.

As the representative examples of the carboxylic acid (I), there are exemplified tyrosine, N-acetyltyrosine, p-hydroxyphenylglycine, p-hydroxyphenylpyruvic acid, p-hydroxyphenylglyoxylic acid, p-hydroxyphenylglycolic acid and the like.

Suitable examples of the derivative at the carboxy group of the additive as specified above may include ester such as $C_1$–$C_6$ alkyl ester, more preferably $C_1$–$C_3$ alkyl ester (e.g. methyl ester, ethyl ester, propyl ester, etc.) and the like; acid amide and hydrazide. As the representative examples of the said derivative, there are exemplified tyrosine ethyl ester, N-acetyltyrosinamide, 2-acetamido-3-(p-hydroxyphenyl)propionohydrazide, 2-amino-3-(p-hydroxyphenyl)propionohydroxamic acid.

The additives as specified above may be used in the form of salt. The said salts may include an inorganic salt such as sodium salt, potassium salt and the like, an organic salt such as ethanolamine salt, hexylamine salt and the like. Further, in case of A-group of the additive and B-group of the additive having amino group, said additive may be used in the from of salt with acid such as hydrochloric acid.

The method of this invention is conducted by adding at least one additive selected from the compounds as specified above to the fermentation medium.

In the method,of this invention, a mode of adding said additive to the fermentation medium is selected depending upon the nature of an individual strain of the microorganisms to be used, including the mutants thereof, the fermentation conditions (e.g. kind of medium, volume of medium, fermentation temperature, fermentation period, etc.) and the time for adding said additive, and the like. Accordingly, such mode of adding the additive to the fermentation medium can easily be selected according to the knowledge conventional to the skilled in the arts in the antibiotic field.

For example, the preferred embodiment of a mode of adding the additive to the fermentation medium can be explained in the following.

One of preferred one is a mode of adding an additive selected from "A-group of the additive" as specified hereinabove to the fermentation medium. Another preferred one is a mode of adding to the fermentation medium a combination of an additive selected from "A-group of the additive" as specified hereinabove and an additive selected from "B-group of the additive" as specified hereinabove.

In this invention, the fermentation is conducted according to a known method and the equivalent one thereof, for examples, one which is disclosed in literatures, e.g., U.S. Pat. No. 3,923,977 and German Offenlegungsschrift No. 2,242,699.

With regard to such a fermentation method, the following is shown for reference.

The fermentation of this invention is conducted by culturing Nocardicin A-producing microorganism in a nutrient medium, to which the additive as specified above is added in a mode as explained above under aerobic conditions such as submerged culture, shaking culture and the like. The above nutrient medium comprises carbon and nitrogen sources which are assimilable by the microorganism.

The preferred sources of carbon are carbohydrates such as glucose, sucrose, maltose, glycerin, starch and the like.

The preferred sources of nitrogen are organic nitrogen sources such as yeast extracts, peptone, gluten meal, cottonseed meal, soybean meal, corn meal, dried yeast, beef extracts, casein hydrolysate, corn steep liquor, urea and the like, and inorganic nitrogen sources such as ammonium salts (e.g. ammonium nitrate, ammonium sulfate, ammonium phosphate, etc.) and the like.

If desired, there may be added to the medium, mineral salts such as calcium carbonate, sodium or patassium phosphate, magnesium chloride or sulfate and the like.

An amount of "the additive" to be added to the nutrient medium, which is needed to stimulate and enhance the production of Nocardicin A varies depending on kinds of the culture medium and the additive to be added. In general, an amount of the additive is selected from within the range of 10–0.001% (by weight), and preferably of 2–0.001% (by weight).

In case that the additive is added to the nutrient medium in combination of "A-group of the additive" and "B-group of additive", preferred combination ratio of "A-group of the additive" and "B-group of the additive" can be selected from within the range of 1:10–10:1 and more preferably 1:5–5:1.

The fermentation is usually conducted at a temperature about between 20° C and 37° C, preferably about 30° C for a period of 50 hours to 150 hours at pH 5–8, preferably at pH 5.5–7.0.

Nocardicin A produced in the cultured broth can be recovered in a conventional manner such as treatment with adsorbents (e.g. activated charcoal, macroporous nonionic adsorption resin), concentration under reduced pressure, crystallization and the like. With regard to the details of such recovery steps, there are to be referred to the published literatures, e.g. U.S. Pat. No. 3,923,977, German Offenlegungsschrift No. 2,242,699.

Nocardicin A produced in the fermentation broth can be conveniently assayed by bioassay as follows.

A test agar plate is prepared by placing 20 ml. of basal medium (pH 7.2) containing 0.3% of Bacto-Tryptone (trade name, made by DIFCO Laboratories, U.S.A.) and 2.0% of agar into a Petri dish (diameter of dish : 85 mm), and then by placing on said basal medium, 5 ml. of upper medium (pH 7.2) containing 0.3% of Bacto-Tryptone, 0.5 mg. of nicotinic acid, 0.5% of agar and 2% of seed culture ($1 \times 10^8$ cells/ml.) of a pathogenic microorganism to be tested on the basal medium.

A paper disc (diameter of the disc : 8 mm) is soaked in a standard solution of Nocardicin A (an amount of content thereof is fixed in advance) on one hand and a paper disc in a test solution on the other hand. After drying both of the discs to run off the excess solution each of said discs is placed on surface of the test agar plate as prepared above and then said plate is incubated at 30° C for 18 hours.

After the incubation, the diameter of inhibitory zone is measured, by which the content of Nocardicin A in test solution is calculated.

The following examples are given for the purpose of illustrating this invention.

The media to be used in the following examples are as follows:

| (1) Aqueous Seed Medium Ingredient | Concentration (%, by weight) |
|---|---|
| Sucrose | 2 |
| Cottonseed meal | 2 |
| Dried yeast | 1 |
| $KH_2PO_4$ | 2.18 |
| $Na_2HPO_4 \cdot 12H_2O$ | 1.43 |
| | (adjusted to pH 6.0) |
| (2) Aqueous Production Medium (I) Ingredient | Concentration (%, by weight) |
| Soluble starch | 2 |
| Yeast extract | 0.4 |
| $KH_2PO_4$ | 0.35 |
| $Na_2HPO_4 \cdot 12H_2O$ | 0.15 |
| $MgSO_4 \cdot 7H_2O$ | 0.1 |
| | (adjusted to pH 6.0) |
| (3) Aqueous Production Medium (II) Ingredient | Concentration (%, by weight) |
| Soluble starch | 1 |
| Glucose | 0.5 |

| -continued | |
|---|---|
| Peptone | 1 |
| Yeast extract | 0.2 |
| Calcium pantothenate | 0.02 |
| $KH_2PO_4$ | 1.8 |
| $Na_2HPO_4 \cdot 12H_2O$ | 1.2 |
| $M_gSO_4 \cdot 7H_2O$ | 0.5 |
| | (adjusted to pH 6.0) |

| (4) Aqueous Production Medium (III) | Concentration |
|---|---|
| Ingredient | (%, by weight) |
| Starch | 1 |
| Cottonseed meal | 2 |
| Dried Yeast | 2 |
| $KH_2PO_4$ | 2.18 |
| $Na_2HPO_4 \cdot 12H_2O$ | 1.43 |
| $M_gSO_4 \cdot 7H_2O$ | 0.5 |
| | (adjusted to pH 6.0) |

EXAMPLE 1

The Aqueous Seed Medium (100 ml.) was poured into each of 10 500 ml. Sakaguchi flasks and sterilized at 120° C for 20 minutes. A loopful of slant culture of *Nocardia uniformis* subsp. tsuyamanensis ATCC 21806 was inoculated into each of the media and cultured at 30° C for 48 hours.

On the other hand, an aqueous medium (20 liters) which was prepared by adding 0.2% of L-tyrosine and 0.2% of glycine (by weight) to the Aqueous Production Medium (III), was poured into 30 liter, jar fermenter and sterilized at 120° C for 20 minutes. To the medium, there was added whole volume of the seed culture as prepared above. The organism was grown at 30° C for 6 days. During the growth period, the broth was stirred at 270 r.p.m. and sterile air was blown through the broth in the ratio of 20 liters per minutes.

Subsequently, the resultant cultured broth was adjusted to pH 4.0 with diluted hydrochloric acid and then filtered with the aid of 6% diatomaceous earth (by weight). A part of the filtrate (3 liters) was passed through a column of Diaion HP 20. After the column was washed with water, Nocardicin A was eluted with 20% aqueous methanol to give an eluate (3 liters), which was concentrated under reduced pressure.

The residue thus obtained was adjusted to pH 2.5 and allowed to stand to give crystals, which was separated by filtration and dried to give colorless crystals (2.9 g.) of Nocordicin A.

I.R. spectrum of the above crystals was identical with that of authentic sample of Nocardicin A.

EXAMPLE 2

The Aqueous Seed Medium (50 ml.) was poured into a 500 ml. Sakaguchi flask and sterilized at 120° C for 20 minutes. A loopful of slant culture of *Nocardia uniformis* subsp. tsuyamanensis ATCC 21806 was inoculated into the medium, and then the organism was grown on a shaker at 30° C for 48 hours.

For the second stage, an aqueous medium (10 ml.) which was prepared by adding a prescribed compound in a prescribed concentration to the Aqueous Production Medium (I), was poured into each of 50 ml. Erlenmeyer flasks and sterilized at 120° C for 20 minutes. Into each of the media, there was inoculated the seed culture (0.5 ml.) as prepared above. The organism was grown on a shaker at 30° C for 6 days. After the fermentation was completed, production of Nocardicin A was confirmed by Rf value showing nearly 0.4 in thin layer chromatography [carrier: Eastman Chromagram Sheet Cellulose No. 6065, developing solvent: a mixture of n-propanol: water (7:3), detection: bioautography using *Pseudomonas aeruginosa* NCTC 10490]. Nocardicin A thus produced in the broths was determined by bioassay using *Pseudomonas aeruginosa* NCTC 10490. The result was shown in the following table 1.

| Additive | Amount of additive (μg/ml) | Production of Nocardicin A (μg/ml) |
|---|---|---|
| L-Tyrosine | 200 | 310 |
|  | 300 | 310 |
| D-Tyrosine | 200 | 365 |
|  | 300 | 410 |
| p-Hydroxyphenyl-pyruvic acid | 200 | 180 |
|  | 300 | 200 |
| D,L-p-Hydroxyphenyl-glycolic acid | 100 | 170 |
|  | 200 | 220 |
| p-Hydroxyphenyl-glyoxylic acid | 100 | 345 |
|  | 200 | 340 |
| L-p-Hydroxy-phenylglycine | 200 | 330 |
|  | 300 | 440 |
| Shikimic acid | 200 | 200 |
|  | 300 | 260 |
| Control | 0 | 110 |

EXAMPLE 3

The Aqueous Seed Medium (50 ml.) was poured into a 500 ml. Sakaguchi flask and sterilized at 120° C for 20 minutes. A loopful of slant culture of *Nocardia uniformis* subsp. tsuyamanensis ATCC 21806 was inoculated into the media and then the organism was grown on a shaker at 30° C for 48 hours.

For the second stage, an aqueous medium (10 ml.) which was prepared by adding a prescribed compound in a prescribed concentration to Aqueous Production Medium (II), was poured into each of 50 ml. Erlenmeyer flasks and sterilized at 120° C for 20 minutes. Into each of the media, there was inoculated the seed culture (0.5 ml.) as prepared above. The organism was grown on a shaker at 30° C for 6 days. After the fermentation was completed, production of Nocardicin A in the broths was confirmed and determined in substantially the same manner as described in Example 2. The results are shown in the following table 2.

Table 2.

| Additive | Amount of additive (μg/ml) | Production of Nocardicin A (μg/ml) |
|---|---|---|
| L-Tyrosine | 125 | 425 |
|  | 250 | 555 |
|  | 500 | 660 |
|  | 1000 | 580 |
| D-Tyrosine | 125 | 445 |
|  | 250 | 555 |
|  | 500 | 530 |
|  | 1000 | 540 |
| p-Hydroxyphenyl-pyruvic acid | 125 | 410 |
|  | 250 | 440 |
|  | 500 | 435 |
| p-Hydroxyphenyl-glyoxylic acid | 125 | 475 |
|  | 250 | 510 |
|  | 500 | 660 |
|  | 1000 | 555 |
| DL-p-Hydroxy-phenylglycine | 250 | 455 |
|  | 500 | 580 |
|  | 1000 | 660 |
| Control | 0 | 370 |

EXAMPLE 4

The Aqueous Seed Medium (50 ml) was poured into a 500 ml. Sakaguchi flash and sterilized at 120° C for 20 minutes. A loopful of slant culture of *Nocardia uniformis* subsp. tsuyamanensis ATCC 21806 was inoculated into the medium and then the organism was grown on a shaker at 30° C for 48 hours.

For the second stage, an aqueous medium (10 ml.) which was prepared by adding a prescribed compound in a prescribed concentration to Aqueous Production Medium (I), was poured into each of 50 ml. Erlenmeyer flasks and sterilized at 120° C for 20 minutes. To each of the media, there was inoculated the seed culture (0.5 ml.), as prepared above. The organism was grown on a shaker at 30° C for 6 days. After the fermentation was completed, production of Nocardicin A in the broths was confirmed and determined in substantially the same manner as described in Example 2. The results are shown in the following table 3.

Table 3

| Additive | Amount of additive (μg/ml) | Production of Nocardicin A (μg/ml) |
| --- | --- | --- |
| L-2-Amino-3-(p-hydroxy-phenyl)propiono-hydroxamic acid | 100 | 190 |
|  | 1000 | 250 |
| N-Acetyl-L-tyrosinamide | 100 | 180 |
|  | 1000 | 300 |
| L-2-Acetoamido-3-(p-hydroxyphenyl)-propionohydrazide | 100 | 120 |
|  | 1000 | 170 |
| N-Acetyl-L-tyrosine | 100 | 150 |
|  | 1000 | 200 |
| L-Tyrosine ethyl ester | 250 | 250 |
|  | 500 | 300 |
|  | 1000 | 250 |
| Control | 0 | 80 |

EXAMPLE 5

The Aqueous Seed Medium (50 ml.) was poured into a 500 ml. Sakaguchi flask and sterilized at 120° C for 20 minutes. A loopful of slant culture of *Nocardia uniformis* subsp. tsuyamanensis ATCC 21806 was inoculated into the medium and then the organism was grown on a shaker at 30° C for 48 hours.

For the second stage, an aqueous medium (10 ml.), which was prepared by adding a prescribed compound in a final concentration of 600 μg/ml to Aqueous Production Medium (I) containing L-tyrosine in a final concentration of 300 μg/ml, was poured into each of 50 ml. Erlenmeyer flasks and sterilized at 120° C for 20 minutes. To each of the media, there was added the seed culture (0.5 ml), as prepared above. The organism was grown on a shaker at 30° C for 6 days. After the fermentation was completed, production of Nocardicin A in each of the broths was confirmed and determined in substantially the same manner as described in Example 2. The results are shown in the following table 4.

Table 4

| Additive | Production of Nocardicin A (μg/ml) |
| --- | --- |
| Glycine | 525 |
| L-Alanine | 470 |
| L-Serine | 490 |
| L-Homoserine | 440 |
| D,L-α-Aminobutyric acid | 525 |
| L-α, β-Diaminopropionic acid | 455 |
| Control | 310 |

EXAMPLE 6

The Aqueous Seed Medium (50 ml.) was poured into a 500 ml. Sakaguchi flask and sterilized at 120° C for 20 minutes. A loopful of slant culture of *Nocardia uniformis* subsp. tsuyamanensis ATCC 21806 was inoculated into the medium and then the organism was grown on a shaker at 30° C for 48 hours.

For the second stage, an aqueous medium (10 ml.) which was prepared by adding a prescribed compound in a prescribed concentration to Aqueous Production Medium (III), was poured into each of 50 ml. Erlenmeyer flasks and sterilized at 120° C for 20 minutes. Into each of the media, there was inoculated the seed culture (0.5 ml.), as prepared above. The organism was grown on a shaker at 30° C for 6 days. After the fermentation was completed, production of Nocardicin A in each of the broths was confirmed and determined in substantially the same manner as described in Example 2. The results are shown in the following table 5.

Table 5

| Addition amount of L-tyrosine (%) | Addition amount of glycine (%) | Production of Nocardicin A (μg/ml) |
| --- | --- | --- |
| 0 | 0 | 540 |
| 0 | 0.1 | 550 |
| 0.1 | 0 | 900 |
| 0.1 | 0.1 | 950 |
| 0.1 | 0.2 | 1000 |
| 0.2 | 0 | 930 |
| 0.2 | 0.1 | 1000 |
| 0.2 | 0.2 | 1200 |
| 0.3 | 0 | 950 |
| 0.3 | 0.1 | 1000 |
| 0.3 | 0.2 | 1100 |

EXAMPLE 7

The Aqueous Seed Medium (50 ml.) was poured into a 500 ml. Sakaguchi flask and sterilized at 120° C for 20 minutes. A loopful of slant culture of *Nocardia uniformis* subsp. tsuyamanensis ATCC 21806 was inoculated into the medium and then the organism was grown on a shaker at 30° C for 48 hours.

For the second stage, an aqueous medium (10 ml.), which was prepared by adding a prescribed compound in a final concentration of 600 μg/ml to Aqueous Production Medium (I), was poured into each of 50 ml. Erlenmeyer flasks and sterilized at 120° C for 20 minutes. To each of the media, there was inoculated the seed culture (0.5 ml.), as prepared above. The organism was grown on a shaker at 30° C for 6 days. After the fermentation was completed, production of Nocardicin A in each of the broths was confirmed and determined in substantially the same manner as described in Example 2. The results are shown in the following table 6.

Table 6

| Additive | Production of Nocardicin A (μg/ml) |
| --- | --- |
| Glycine | 170 |
| L-Alanine | 170 |
| D,L-α-Amino butyric acid | 180 |
| L-α,β-Diamino propianic acid | 180 |
| None | 160 |

We claim:

1. In the process for preparing Nocardicin A by culturing *Nocardia uniformis* subsp. tsuyamanensis in a fermentation medium, the improvement which comprises, to the fermentation medium, adding at least one additive selected from shikimic acid, a carboxylic acid of the formula:

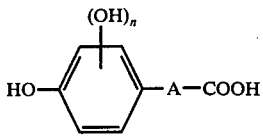

wherein
A is alkylene group having hydroxy, amino, acylamino or oxo group, and
n is an integer of 0–4;
glycine, alanine, serine, homoserine, α-aminobutyric acid and α,β-diaminopropionic acid; and their ester, acid amide and hydrazide derivatives at the carboxy in a concentration of 2–0.001% by weight.

2. The process according to claim 1, in which there is added, to the fermentation medium, a combination of an additive selected from skikimic acid and a carboxylic acid of the formula (I) and their ester, acid amide and hydrazide derivatives at the carboxy and an additive selected from glycine, alanine, serine, homoserine, α-aminobutyric acid and α,β-diaminopropionic acid, and their ester, acid amide and hydrazide derivatives at the carboxy.

3. The process according to claim 1, in which there is added, to the fermentation medium, an additive selected from shikimic acid and a carboxylic acid of the formula (I), and their ester, acid amide and hydrazide derivatives at the carboxy.

4. The process according to claim 3, in which the additive is shikimic acid or their defined derivatives at the carboxy.

5. The process according to claim 3, in which the additive is a carboxylic acid of the formula (I) or their defined derivatives at the carboxy.

6. The process according to claim 5, in which the additive is a carboxylic acid of the formula (I) wherein A is alkylene group having amino group; and n is 0.

7. The process according to claim 6, in which the carboxylic acid is tyrosine.

8. The process according to claim 6, in which the carboxylic acid is p-hydroxyphenylglycine.

9. The process according to claim 5, in which the additive is a carboxylic acid of the formula (I) wherein A is alkylene group having hydroxy group; and n is 0.

10. The process according to claim 9, in which the carboxylic acid is p-hydroxyphenylglycolic acid.

11. The process according to claim 5, in which the additive is a carboxylic acid of the formula (I) wherein A is alkylene group having acylamino group; and n is 0.

12. The process according to claim 11 wherein the alkylene group is alkanoylamino.

13. The process according to claim 5, in which the additive is a carboxylic acid of the formula (I) wherein A is alkylene group having oxo group; and n is 0.

14. The process according to claim 13, in which the carboxylic acid is p-hydroxphenyl pyruvic acid.

15. The process according to claim 13, in which the carboxylic acid is p-hydroxyphenylglyoxylic acid.

16. The process according to claim 5, in which the derivative is an ester of a carboxylic acid of formula (I).

17. The process according to claim 16, in which the ester is an alkyl ester.

18. The process according to claim 17, in which the alkyl ester is tyrosine ethyl ester.

19. The process according to claim 5, in which the derivative is an amide of a carboxylic acid of formula (I).

20. The process according to claim 19, in which the amide is N-acetyltyrosinamide.

21. The process according to claim 19, in which the additive is 2-amino-3-(p-hydroxyphenyl)propionohydroxamic acid.

22. The process according to claim 5, in which the derivative is a hydrazide of a carboxylic acid of formula (I).

23. The process according to claim 22, in which the hydrazide is 2-acetamido-3-(p-hydroxyphenyl)propionohydrazide.

24. The process according to claim 2, in which the combination of the additives consists of tyrosine and glycine.

25. The process according to claim 2, in which the combination of the additives consists of tyrosine and serine.

26. The process according to claim 2, in which the combination of the additives consists of tyrosine and homoserine.

27. The process according to claim 2, in which the combination of the additives consists of tyrosine and α-aminobutyric acid.

28. The process according to claim 2, in which the combination of the additives consists of tyrosine and α,β-diaminopropionic acid.

29. The process according to claim 12, in which the carboxylic acid is N-acetyltyrosine.

* * * * *

UNITED STATES PATENT OFFICE
CERTIFICATE OF CORRECTION

PATENT NO. : 4,110,166

DATED : August 29, 1978

INVENTOR(S) : Shigeru Mori, Shigeyoshi Ohsawa, Hatsuo Aoki and Hiroshi Imanaka

It is certified that error appears in the above-identified patent and that said Letters Patent are hereby corrected as shown below:

Claim 4, line 2, delete "their".

Claim 5, line 2, delete "their".

Signed and Sealed this

Tenth Day of April 1979

[SEAL]

Attest:

RUTH C. MASON
Attesting Officer

DONALD W. BANNER
Commissioner of Patents and Trademarks